United States Patent
Funakoshi et al.

(10) Patent No.: US 7,214,815 B2
(45) Date of Patent: May 8, 2007

(54) METALLIC COPPER CATALYST FOR POLYFLUOROALKYLETHYL IODIDE PRODUCTION AND PROCESS FOR PRODUCING POLYFLUOROALKYLETHYL IODIDE

(75) Inventors: Yoshirou Funakoshi, Settsu (JP); Jun Miki, Settsu (JP)

(73) Assignee: Daikin Industries, Ltd., Osaka (JP)

( * ) Notice: Subject to any disclaimer, the term of this patent is extended or adjusted under 35 U.S.C. 154(b) by 76 days.

(21) Appl. No.: 10/516,940

(22) PCT Filed: Jun. 17, 2003

(86) PCT No.: PCT/JP03/07643

§ 371 (c)(1),
(2), (4) Date: Dec. 15, 2004

(87) PCT Pub. No.: WO03/106023

PCT Pub. Date: Dec. 24, 2003

(65) Prior Publication Data

US 2005/0250966 A1    Nov. 10, 2005

(30) Foreign Application Priority Data

Jun. 17, 2002    (JP)    ............... 2002-175381

(51) Int. Cl.
*C07C 69/52*    (2006.01)
*C07C 17/00*    (2006.01)
*C07C 17/266*    (2006.01)

(52) U.S. Cl. ................ 560/205; 570/139; 570/172

(58) Field of Classification Search ........ 570/172, 570/139; 560/205
See application file for complete search history.

(56) References Cited

U.S. PATENT DOCUMENTS 3,557,224 A    1/1971    Jaeger et al.
3,979,469 A    9/1976    Jager .................. 260/653
4,587,366 A    5/1986    von Werner ........... 570/172
4,650,913 A    3/1987    Feiring ................. 570/144
5,639,923 A    6/1997    Von Werner ........... 570/139

FOREIGN PATENT DOCUMENTS

| GB | 1415245 | 11/1975 |
|----|---------|---------|
| GB | 1415245 A | 11/1975 |
| JP | 39-18112 | 8/1964 |
| JP | 44-21086 | 9/1969 |
| JP | 2002-316956 | 10/2002 |
| JP | 2002-316957 | 10/2002 |
| JP | 2003-183190 | 7/2003 |

OTHER PUBLICATIONS

Brace; "Syntheses with perfluoroalkyl radicals from perfluoroalkyl iodides. A rapid survey of synthetic possibilities with emphasis on practical applications. Part one: alkenes, alkynes and allylic compounds"; J. of Fluorine Chemistry 93 (1999) pp. 1-25. (See specification).

Chen et al; "Copper-Induced telomerization of Tetrafluoroethylene with Fluoroalkyl Iodides"; J. Fluorine Chemistry 36 (1987) pp. 483-489. (See Specification).

Von Werner; "Reactions of perfluoroalkyl iodides with CC-multiple bonds induced by transition metal centers"; J. Fluorine Chemistry 28 (1985) pp. 229-233. (See Specification).

International Search Report dated Sep. 2, 2003.

*Primary Examiner*—J. Parsa
(74) *Attorney, Agent, or Firm*—Armstrong, Kratz, Quintos, Hanson & Brooks, LLP

(57) ABSTRACT

The present invention provides a metallic copper catalyst for use in an ethylene addition reaction to polyfluoroalkyl iodides, a process for efficiently producing a polyfluoroalkylethyl iodide using such a metal copper catalyst in an ethylene addition reaction to a polyfluoroalkyl iodide, and a process for efficiently producing a polyfluoroalkylethyl iodide from a polyfluoroalkyl iodide using the same metallic copper catalyst in a telomerization reaction and a subsequent ethylene addition reaction.

7 Claims, No Drawings

METALLIC COPPER CATALYST FOR POLYFLUOROALKYLETHYL IODIDE PRODUCTION AND PROCESS FOR PRODUCING POLYFLUOROALKYLETHYL IODIDE

TECHNICAL FIELD

The present invention relates to a process for producing a polyfluoroalkylethyl iodide from a polyfluoroalkyl iodide and ethylene using a metallic copper catalyst.

BACKGROUND OF THE INVENTION

Fluorine-containing alkyl iodides have a broad range of applications as ingredients for producing a variety of products such as surfactants, pharmaceuticals, functional polymers, etc.

In particular, compounds obtained by an ethylene addition reaction between the iodine atom and the polyfluoro alkyl group of polyfluoroalkyl iodides (such compounds are hereinafter referred to as polyfluoroalkylethyl iodides) can be converted to various other compounds since the iodine therein can be more readily substituted by a nucleophile compared with the iodine contained in polyfluoroalkyl iodides. Therefore, polyfluoroalkylethyl iodides have drawn attention as ingredients for a broad range of products.

As an example of a process for producing such polyfluoroalkylethyl iodides, a process employing an ethylene addition reaction to polyfluoroalkyl iodides (hereinafter simply referred to as an "ethylene addition reaction") as shown below is known:

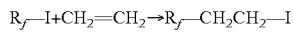

$$R_f\text{—I} + CH_2\!=\!CH_2 \rightarrow R_f\text{—}CH_2CH_2\text{—I}$$

wherein $R_f$ is a $C_{1-6}$ polyfluoroalkyl.

In connection with such ethylene addition reactions, processes employing ruthenium/activated carbon (Ru/C), platinum/activated carbon (Pt/C), silver/alumina (Ag/Al$_2$O$_3$) and like noble metals as catalysts (Konrad von Werner, *Journal of Fluorine Chemistry* 28(1985): 229–233); processes employing azobisisobutyronitrile (AIBN) or benzoyl peroxide and like organic peroxides as catalysts (Neal O. Brace, *Journal of Fluorine Chemistry* 93(1999): 1–25); etc., have been reported. However, noble metals have the disadvantage that they are expensive and thus result in high production costs. Organic peroxides are also expensive and for one-time use only, resulting in high production costs. Furthermore, organic peroxides are disadvantageous in that they are hazardous per se and cause inclusion of impurities in the reaction product. Meanwhile, ethylene addition reactions conducted in the presence of metallic copper catalysts have not been reported.

As an example of a process for producing starting material polyfluoroalkyl iodides, the telomerization reaction conducted in the presence of a copper catalyst as shown below (hereinafter simply referred to as a "telomerization reaction") is known (Japanese Unexamined Patent Publication No. 239336/1996; Qing-Yun Chen, et al., *Journal of Fluorine Chemistry* 36(1987): 483–489; etc.):

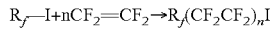

$$R_f\text{—I} + nCF_2\!=\!CF_2 \rightarrow R_f(CF_2CF_2)_n I$$

wherein $R_f$ is a $C_{1-6}$ polyfluoroalkyl and n is an integer from 1 to 8.

It has not been reported that such a telomerization reaction and the aforementioned ethylene addition reaction can be successively conducted using the same catalyst. If these reactions can be successively conducted in the presence of the same catalyst, simplification of the production process and reduction in production cost are to be expected.

DISCLOSURE OF THE INVENTION

An object of the present invention is to provide a metallic copper catalyst for use in an ethylene addition reaction to a polyfluoroalkyl iodide and a process for efficiently producing a polyfluoroalkylethyl iodide using such a metal copper catalyst in an ethylene addition reaction to a polyfluoroalkyl iodide.

Another object of the present invention is to provide a process for efficiently producing a polyfluoroalkylethyl iodide from a polyfluoroalkyl iodide using the same metallic copper catalyst in a telomerization reaction and a subsequent ethylene addition reaction.

Yet another object of the present invention is to provide a process for efficiently producing a useful polyfluoroalkylethyl acrylate by reacting the polyfluoroalkylethyl iodide obtained according to the aforementioned production process with an acrylic acid salt or the like.

The inventors conducted extensive research to solve the problems described above and found a process for producing a polyfluoroalkylethyl iodide employing an ethylene addition reaction in the presence of a metallic copper catalyst. The present invention was accomplished by conducting further research based on this finding.

In particular, the present invention relates to the following:

Item 1. A metallic copper catalyst for use in an ethylene addition reaction to provide a polyfluoroalkylethyl iodide from a polyfluoroalkyl iodide and ethylene.

Item 2. The metallic copper catalyst according to Item 1, wherein the polyfluoroalkyl iodide is a compound represented by Formula (I):

$$R_f\text{—I} \qquad (I)$$

wherein $R_f$ is a $C_{1-6}$ polyfluoroalkyl; and the polyfluoroalkylethyl iodide is a compound represented by Formula (II):

$$R_f\text{—}CH_2CH_2\text{—I} \qquad (II)$$

wherein $R_f$ is as defined above.

Item 3. A process for producing a polyfluoroalkylethyl iodide represented by Formula (II):

$$R_f\text{—}CH_2CH_2\text{—I} \qquad (II)$$

wherein $R_f$ is a $C_{1-6}$ polyfluoroalkyl, the process comprising the step of reacting ethylene with a compound represented by Formula (I):

$$R_f\text{—I} \qquad (I)$$

wherein $R_f$ is as defined above, in the presence of a metallic copper catalyst.

Item 4. The process according to Item 3, wherein the metallic copper catalyst is a powdery metallic copper or a metallic copper supported on a carrier, and the reaction is conducted at a temperature of 50–200° C. under a pressure of 0.01–3 MPa.

Item 5. A process for producing polyfluoroalkylethyl iodide (IV), the process comprising steps (a) and (b) conducted in the presence of the same metallic copper catalyst:

(a) a step of reacting tetrafluoroethylene with a compound represented by Formula (I):

$$R_f\text{—I} \quad (I)$$

wherein $R_f$ is a $C_{1-6}$ polyfluoroalkyl, to produce a compound represented by Formula (III):

$$R_f(CF_2CF_2)_n I \quad (III)$$

wherein n is an integer from 1 to 8 and $R_f$ is as defined above; and (b) a step of reacting ethylene with compound (III) obtained in step (a) to produce a polyfluoroalkylethyl iodide represented by Formula (IV):

$$R_f(CF_2CF_2)_n CH_2CH_2 I \quad (IV)$$

wherein $R_f$ and n are as defined above.

Item 6. A process for producing polyfluoroalkylethyl acrylate (VI), the process comprising steps (a), (b) and (c), steps (a) and (b) being conducted in the presence of the same metallic copper catalyst:

(a) a step of reacting tetrafluoroethylene with a compound represented by Formula (I):

$$R_f\text{—I} \quad (I)$$

wherein $R_f$ is a $C_{1-6}$ polyfluoroalkyl, to produce a compound represented by Formula (III):

$$R_f(CF_2CF_2)_n I \quad (III)$$

wherein n is an integer from 1 to 8 and $R_f$ is as defined above;

(b) a step of reacting ethylene with compound (III) obtained in step (a) to produce a compound represented by Formula (IV):

$$R_f(CF_2CF_2)_n CH_2CH_2 I \quad (IV)$$

wherein $R_f$ and n are as defined above; and (c) a step of reacting compound (IV) obtained in step (b) with a carboxylate represented by Formula (V):

$$CH_2=C(X)COOM \quad (V)$$

wherein X is H or $CH_3$ and M is an alkali metal, to produce a polyfluoroalkylethyl acrylate represented by Formula (VI):

$$R_f(CF_2CF_2)_n CH_2CH_2 OCOC(X)=CH_2 \quad (VI)$$

wherein $R_f$, n and X are as defined above.

Item 7. A process for producing a polyfluoroalkylethyl acrylate represented by Formula (VII):

$$R_f CH_2CH_2 OCOC(X)=CH_2 \quad (VII)$$

wherein $R_f$ is a $C_{1-6}$ polyfluoroalkyl, and X is H or $CH_3$, the process comprising reacting a polyfluoroalkylethyl iodide obtained according to the production process of Item 3 and represented by Formula (II):

$$R_f\text{—}CH_2CH_2\text{—}I \quad (II)$$

wherein $R_f$ is as defined above, with a carboxylate represented by Formula (V):

$$CH_2=C(X)COOM \quad (V)$$

wherein X is as defined above, and M is an alkali metal.

The present invention is described in more detail below.

Process for Producing polyfluoroalkylethyl iodide (II)

A process for producing polyfluoroalkylethyl iodide (II) using the metallic copper catalyst of the present invention is described. This process is for producing a compound represented by Formula (II):

$$R_f\text{—}CH_2CH_2\text{—}I \quad (II)$$

wherein $R_f$ is a $C_{1-6}$ polyfluoroalkyl, the process comprising reacting ethylene with a compound represented by Formula (I):

$$R_f\text{—}I \quad (I)$$

wherein $R_f$ is as defined above, in the presence of a metallic copper catalyst.

The metallic copper catalyst of the invention is not limited insofar as it is a copper metal. In view of catalytic activity, the form of the metallic copper catalyst of the invention is preferably powdery, which ensures a large contact area with the starting materials on the surface of the metallic copper. The average particle diameter of the powdery copper is, for example, about 0.1 to about 300 μm, and preferably about 30 to about 150 μm.

It is sufficient that the metallic copper catalyst is used in an amount of, for example, about 0.1 to about 90 wt. %, preferably about 0.5 to about 10 wt. %, based on the weight of compound (I).

Moreover, the metallic copper catalyst of the present invention may be a catalyst in which metallic copper is supported on a carrier. Usable carriers are not limited insofar as the activity of the metallic copper catalyst is not adversely affected, and examples thereof include metal oxides. Specific examples are single-metal oxides selected from the group consisting of zinc oxide, iron oxide, copper oxide, titanium oxide, zirconium oxide, cerium oxide, aluminum oxide and silicon oxide; complex oxides comprising 2 or more metal elements selected from the group consisting of zinc, iron, copper, titanium, zirconium, cerium, aluminum and silicon; etc. Although the form of carrier supporting the metallic copper catalyst is not limited, it is preferably powdery in view of catalytic activity. The metallic copper can be supported on the carrier according to known methods.

The amount of metallic copper in a metallic copper catalyst wherein the metallic copper is supported on a carrier is about 0.01 to about 50 wt. %, preferably about 0.1 to about 20 wt. %, based on the total amount of catalyst.

A metallic copper catalyst in which metallic copper is supported on a carrier is used in an amount of, for example, about 0.1 to about 90 wt. %, preferably about 0.5 to about 10 wt. %, based on the weight of compound (I).

Other metals may be used with the metallic copper catalyst of the present invention to enhance its catalytic activity. Examples thereof include titanium, chromium, iron, cobalt, nickel, tin, etc. Among such other metals, tin is preferable. Such other metals are used in an amount of, for example, about 0.1 to about 90 wt. % relative to the weight of the metallic copper catalyst, and preferably about 10 to about 30 wt. %. They are preferably powdery in view of catalytic activity.

Examples of polyfluoroalkyls represented by $R_f$ include $C_{1-6}$ linear or branched perfluoroalkyls and alkyls wherein at least one hydrogen atom contained in $C_{1-6}$ linear or branched alkyls are substituted with fluorine. Specific examples are $CF_3$, $C_2F_5$, n-$C_3F_7$, i-$C_3F_7$, n-$C_4F_9$, i-$C_4F_9$, sec-$C_4F_9$, tert-$C_4F_9$, n-$C_5F_{11}$, i-$C_5F_{11}$, n-$C_6F_{13}$, i-$C_6F_{13}$ and like perfluoroalkyls; and $CHF_2(CF_2)_m$ (m is an integer from 1 to 5), $CH_2F(CF_2)_m$ (m is an integer from 1 to 5) and like alkyls wherein fluorine atom(s) substitute hydrogen atom(s) contained in the alkyl group. These compounds may be prepared according to known methods.

Compound (I) may be reacted with ethylene gas under pressure in the presence of the metallic copper catalyst. The ethylene gas pressure is, for example, about 0.01 to about 3 MPa, and preferably about 0.1 to about 1 MPa. Ethylene gas is used in an amount of, for example, about 1 to about 1.2 mol per mol of Compound (I).

The reaction can be conducted by, for example, introducing compound (I) and the metallic copper catalyst into an autoclave or like a reactor for pressurizing and heating; deaerating the reactor; raising the temperature by a heater to the reaction temperature; introducing ethylene gas into the reactor; and stirring at that temperature for a specific period of time. The reaction temperature is, for example, about 50 to about 200° C., preferably about 70 to 120° C., in view of safety and reaction speed. In this reaction, as ethylene is consumed, the pressure in the reactor decreases. It is preferable to keep the pressure constant by supplying ethylene as and when necessary because low pressures in the reactor result in slow reaction speeds. In this reaction, the end point is determined to be when no ethylene pressure decrease is observed. Although the reaction time varies depending on the reaction conditions, it is usually about 0.5 to about 4 hours.

The reaction is afforded a high conversion rate by the use of the aforementioned metallic copper catalyst. Moreover, it gives a monoethylene adduct with a high selectivity. Furthermore, since the aforementioned metallic copper catalyst is a solid catalyst, it has the advantage that it can be readily separated from the reaction product and reused.

Process for Producing polyfluoroalkylethyl iodide (IV)

Next, described is a process for producing polyfluoroalkylethyl iodide (IV) employing a telomerization reaction and an ethylene addition reaction, both of which are conducted in the presence of the metallic copper catalyst of the present invention.

The telomerization reaction refers to a reaction to produce a compound represented by Formula (III):

$$R_f(CF_2CF_2)_nI \qquad (III)$$

wherein n is an integer from 1 to 8 and $R_f$ is a $C_{1-6}$ polyfluoroalkyl, by reacting tetrafluoroethylene with a compound represented by Formula (I):

$$R_f-I \qquad (I)$$

wherein $R_f$ is as defined above.

Specific examples of polyfluoroalkyls represented by $R_f$ contained in starting compound (I) are as described above.

Metallic copper catalysts usable are those described in relation to the ethylene addition reaction above.

The reaction may be conducted according to known methods. The reaction may be carried out by, for example, introducing compound (I) and the metallic copper catalyst into an autoclave or like a reactor for heating and pressuring; deaerating the reactor; raising the temperature by a heater to about 80 to about 140° C.; introducing tetrafluoroethylene gas into the reactor; maintaining the pressure in the reactor at about 0.3 to about 1.2 MPa; and stirring at that temperature and pressure for a specific period of time.

After the telomerization reaction, the telomeric reaction product may be successively subjected to the aforementioned ethylene addition reaction in the same reactor without isolation. The metallic copper catalyst used in the telomerization reaction can be used as it is in the following ethylene addition reaction. When the ethylene addition reaction is successively performed after the telomerization reaction, it is preferable to remove tetrafluoroethylene and dearate the reactor before the ethylene addition reaction.

Alternatively, after the telomerization reaction, the telomeric reaction product may be isolated and then subjected to the following ethylene addition reaction. In this case, telomers with a low polymerization degree (e.g., those having 6 or fewer carbons atoms) are preferably separated by distillation for recycling.

Using the production process comprising a series of steps of the present invention, compound (IV) can be efficiently produced from compound (I) in one sequence.

Process for Producing polyfluoroalkylethyl acrylate (VI) or (VII)

Described here is a process for producing polyfluoroalkylethyl acrylate (VI) or (VII), which is used as an ingredient for, e.g., water- and oil-repelling polymers, after the telomerization and ethylene addition reactions using the metallic copper catalyst of the invention.

This process refers to a process for producing a compound represented by Formula (VI):

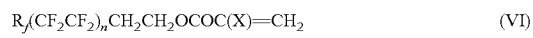
$$R_f(CF_2CF_2)_nCH_2CH_2OCOC(X)=CH_2 \qquad (VI)$$

wherein $R_f$ and n are as defined above and X is H or $CH_3$, by reacting a carboxylate represented by Formula (V):

$$CH_2=C(X)COOM \qquad (V)$$

wherein X is as defined above and M is an alkali metal, with compound (IV) obtained according to the aforementioned telomerization and ethylene addition reactions.

The reaction between compound (IV) and carboxylate (V) may be carried out by, for example, mixing compound (IV) with carboxylate (V) in an alcoholic solvent (e.g., amyl alcohol, t-butanol, 2-propanol or the like) under ordinary pressure, heating while stirring at usually about 150 to about 200° C. for about 4 to about 12 hours, and separating polyfluoroalkylethyl acrylate (VI) from the reaction mixture.

Examples of alkali metals represented by M include sodium, potassium, etc. Among these, potassium is preferable in view of reactivity.

Meanwhile, by reacting polyfluoroalkylethyl iodide (II) obtained by the previously-mentioned production process with carboxylate (V) under the conditions described above, another polyfluoroalkylethyl acrylate represented by Formula (VII):

$$R_fCH_2CH_2OCOC(X)=CH_2 \qquad (VII)$$

wherein $R_f$, n and X are as defined above can be prepared.

Using the production process comprising a series of steps of the present invention, compound (VI) or (VII), both of which are useful as ingredients for water- and oil-repelling polymers, can be efficiently produced from compound (I).

BEST MODE FOR CARRYING OUT THE INVENTION

Examples are given below to illustrate the invention in more detail, but the scope of the invention is not limited to these examples.

EXAMPLE 1 (ETHYLENE ADDITION REACTION)

Into a 200 ml Hastelloy (registered trademark) autoclave were introduced 138.6 g of perfluoroethyl iodide ($CF_3CF_2I$) and 8.21 g of copper powder (average particle diameter: 45 μm, manufactured by Mitsui Mining & Smelting Co., Ltd.). The autoclave was deaerated, and the temperature was raised to 80° C. Ethylene was charged into the autoclave to an inner pressure of 1.0 MPa. As the perfluoroethyl iodide is consumed, the pressure in the autoclave is decreased and the partial pressure of the ethylene is increased. Therefore, to maintain the aforementioned pressure, ethylene was charged while monitoring the pressure. The time at which no ethylene pressure decrease was observed was determined as the end point of the reaction. The reaction time was 80 minutes. After cooling the reaction mixture, the reaction product was analyzed by gas chromatography (GC).

The conversion of the perfluoroethyl iodide was 99.5%, and the selectivity for the resulting ethylene adduct (adduct of one ethylene molecule) was 99.8%.

(GC Conditions)

Column: SE-30 3 m
Detector: TCD 100 mA
Carrier gas: helium 50 ml/min
Temperature of the inlet (injection port) and the detector: 250° C.
Conditions for temperature increase: 50° C. (no retention) →10° C./min→250° C. (10-minute retention)

Column: Pora-Q 3 m
Detector: TCD 100 mA
Carrier gas: helium 50 ml/min
Temperature of the inlet (injection port) and the detector: 250° C.
Conditions for temperature increase: 50° C. (no retention) →20° C./min→250° C. (10-minute retention)

When a polyfluoroalkyl iodide having 1–4 carbon atoms was used as a starting material, the Pora-Q column was used. When a polyfluoroalkyl iodide having at least 5 carbon atoms was used as a starting material, the SE-30 column was used.

EXAMPLES 2–6 (ETHYLENE ADDITION REACTION)

Reactions were conducted in the same manner as in Example 1 except that the perfluoroethyl iodide was replaced with 1-iodoperfluorooctane (n-$C_8F_{17}$I).

After cooling the reaction mixtures, the reaction products were analyzed by gas chromatography (GC). Table 1 shows the results.

COMPARATIVE EXAMPLE 1 (ETHYLENE ADDITION REACTION)

A reaction was conducted in the same manner as in Example 1 except that the perfluoroethyl iodide and the copper catalyst were replaced with 1-iodoperfluorooctane (n-$C_8F_{17}$I) and an organic peroxide, i.e., t-butylperoxyisopropyl monocarbonate (Perbutyl I, manufactured by NOF Corporation), respectively.

After cooling the reaction mixture, the reaction product was analyzed by gas chromatography (GC). Table 1 shows the results.

TABLE 1

| | n-$C_8F_{17}$I g | Copper catalyst g (wt. % *) | Reaction temperature ° C. | Ethylene pressure MPa | Reaction time Min | Conversion GC % |
|---|---|---|---|---|---|---|
| Ex. 2 | 132 | 13.4 (10) | 80 | 0.1 | 105 | 99.94 |
| Ex. 3 | 130.8 | 2.66 (2) | 80 | 0.1 | 120 | 99.71 |
| Ex. 4 | 125.3 | 2.51 (2) | 80 | 0.55 | 58 | 99.89 |
| Ex. 5 | 155.2 | 3.11 (2) | 120 | 0.1 | 56 | 99.97 |
| Ex. 6 | 122.5 | 0.62 (0.5) | 120 | 0.55 | 40 | 99.86 |
| Comp. Ex. 1 | 133.2 | 0.13 ** | 105 | 0.1–0.2 | 180 | 97.7 |

* wt. % relative to n-$C_8F_{17}$I
** conducted using t-butylperoxyisopropyl monocarbonate (Perbutyl I) as a catalyst The conversion of each 1-iodoperfluorooctane of Examples 2–6 was more than 99.7%. The selectivity for the resulting ethylene adduct (adduct of one ethylene molecule) was 99.9% or greater in each case.

EXAMPLE 7 (TELOMERIZATION REACTION—ETHYLENE ADDITION REACTION)

(1) Into a stirred tank pressure reactor equipped with a stirrer were introduced 100 g of 1-iodoperfluorobutane (n-$C_4F_9$I) and 4 g of copper powder (325 mesh, manufactured by Kishida Chemical Co.,Ltd.), and the reactor was then heated to 110° C. Tetrafluoroethylene was introduced into the reactor at that temperature, and the pressure in the reactor was increased to 0.38 MPa. Tetrafluoroethylene is consumed as the reaction progresses. Therefore, to maintain the pressure at the aforementioned level, tetrafluoroethylene was supplied as and when necessary while monitoring the reactor pressure. After introducing tetrafluoroethylene to a total of 18 g, the reaction was stopped.

A sample was collected from the reaction mixture in the reactor to analyze the product by gas chromatography (GC). Table 2 shows the results. The conversion was 40.0%.

TABLE 2

| Reaction product distribution: $CF_3CF_2CF_2CF_2(CF_2CF_2)_n$-I | | | | | | |
|---|---|---|---|---|---|---|
| n | 0 | 1 | 2 | 3 | 4 | 5 |
| mol % | 60.0 | 34.5 | 5.1 | 0.63 | 0.072 | 0.009 |

(2) The reactor was deaerated, and the temperature thereof was increased to 80° C. Ethylene was slowly charged into the reactor to an inner pressure of 0.8 MPa. The procedures described in Example 1 were then repeated.

The conversion of the perfluoroethyl iodide was 99.8%, and the selectivity for the resulting ethylene adduct (adduct of one ethylene molecule) was 100%.

INDUSTRIAL APPLICABILITY

According to the production process of the present invention, a polyfluoroalkylethyl iodide can be efficiently produced from a polyfluoroalkyl iodide employing an ethylene addition reaction conducted in the presence of an inexpensive metallic copper catalyst. The use of a metallic copper catalyst allows a low reaction temperature, enabling the catalyst after reaction to be readily separated and reused.

Furthermore, according to the production process of the present invention, since a telomerization reaction and an ethylene addition reaction can be conducted in one sequence using the same metallic copper catalyst, the series of steps for polyfluoroalkylethyl iodide production can be simplified, and the production cost can be reduced accordingly.

The invention claimed is:

1. A composition, comprising:
a metallic copper catalyst;
a polyfluoroalkyl iodide; and
ethylene;
wherein the metallic copper catalyst is present in an amount in the range of 0.5 to 10 wt. % of the polyfluoroalkyl iodide.

2. The composition according to claim 1, wherein the polyfluoroalkyl iodide is a compound represented by Formula (I):

$$R_f\text{—I} \qquad (I)$$

wherein $R_f$ is a $C_{1-6}$ polyfluoroalkyl.

3. A process for producing a polyfluoroalkylethyl iodide represented by Formula (II):

$$R_f\text{—CH}_2\text{CH}_2\text{—I} \qquad (II)$$

wherein $R_f$ is a $C_{1-6}$ polyfluoroalkyl,
the process comprising the step of reacting ethylene with a compound represented by Formula (I):

$$R_f\text{—I} \qquad (I)$$

wherein $R_f$ is as defined above, in the presence of a metallic copper catalyst.

4. The process according to claim 3, wherein the metallic copper catalyst is a powdery metallic copper or a metallic copper supported on a carrier, and the reaction is conducted at a temperature of 50–200° C. under a pressure of 0.01–3 MPa.

5. A process for producing polyfluoroalkylethyl iodide (IV), the process comprising the following steps (a) and (b):
(a) a step of reacting, in the presence of a metallic copper catalyst, tetrafluoroethylene with a compound represented by Formula (I):

$$R_f\text{—I} \qquad (I)$$

wherein $R_f$ is a $C_{1-6}$ polyfluoroalkyl, to produce a compound represented by Formula (III):

$$R_f(CF_2CF_2)_n I \qquad (III)$$

wherein n is an integer from 1 to 8 and $R_f$ is as defined above; and
(b) a step of reacting, in the presence of said metallic copper catalyst, ethylene with compound (III) obtained in step (a) to produce a polyfluoroalkylethyl iodide represented by Formula (IV):

$$R_f(CF_2CF_2)_n CH_2CH_2 I \qquad (IV)$$

wherein $R_f$ and n are as defined above.

6. A process for producing polyfluoroalkylethyl acrylate (VI), the process comprising the following steps (a), (b) and (c):
(a) a step of reacting, in the presence of a metallic copper catalyst, tetrafluoroethylene with a compound represented by Formula (I):

$$R_f\text{—I} \qquad (I)$$

wherein $R_f$ is a $C_{1-6}$ polyfluoroalkyl, to produce a compound represented by Formula (III):

$$R_f(CF_2CF_2)_n I \qquad (III)$$

wherein n is an integer from 1 to 8 and $R_f$ is as defined above;
(b) a step of reacting, in the presence of said metallic copper catalyst, ethylene with compound (III) obtained in step (a) to produce a compound represented by Formula (IV):

$$R_f(CF_2CF_2)_n CH_2CH_2 I \qquad (IV)$$

wherein $R_f$ and n are as defined above; and
(c) a step of reacting compound (IV) obtained in step (b) with a carboxylate represented by Formula (V):

$$CH_2\text{=}C(X)COOM \qquad (V)$$

wherein X is H or $CH_3$ and M is an alkali metal, to produce a polyfluoroalkylethyl acrylate represented by Formula (VI):

$$R_f(CF_2CF_2)_n CH_2CH_2 OCOC(X)\text{=}CH_2 \qquad (VI)$$

wherein $R_f$, n and X are as defined above.

7. A process for producing a polyfluoroalkylethyl acrylate represented by Formula (VII):

$$R_f CH_2CH_2 OCOC(X)\text{=}CH_2 \qquad (VII)$$

wherein $R_f$ is a $C_{1-6}$ polyfluoroalkyl, and X is H or $CH_3$,
the process comprising the step of producing a polyfluoroalkylethyl iodide according to the production process of claim 3 and represented by Formula (II):

$$R_f\text{—CH}_2CH_2\text{—I} \qquad (II)$$

wherein $R_f$ is as defined above, and
the step of reacting said polyfluoroalkylethyl iodide with a carboxylate represented by Formula (V):

$$CH_2\text{=}C(X)COOM \qquad (V)$$

wherein X is as defined above, and M is an alkali metal.

* * * * *